(12) United States Patent
Hollingsworth et al.

(10) Patent No.: US 6,392,110 B1
(45) Date of Patent: May 21, 2002

(54) ORDERED POLYACETYLENES AND PROCESS FOR THE PREPARATION THEREOF

(75) Inventors: Rawle I. Hollingsworth, Haslett; Guijun Wang, East Lansing, both of MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 7 days.

(21) Appl. No.: 09/644,172

(22) Filed: Aug. 23, 2000

Related U.S. Application Data

(62) Division of application No. 09/273,219, filed on Mar. 19, 1999, now Pat. No. 6,194,529.

(51) Int. Cl.$^7$ ................................................ C07C 5/08
(52) U.S. Cl. ........................ 585/325; 585/534; 585/505; 585/538; 585/643
(58) Field of Search ................................ 585/325, 505, 585/534, 538, 643

(56) References Cited

U.S. PATENT DOCUMENTS

| | | |
|---|---|---|
| 4,994,597 A | 2/1991 | Inoue et al. |
| 5,087,751 A | 2/1992 | Inoue et al. |
| 5,292,939 A | 3/1994 | Hollingsworth |
| 5,319,110 A | 6/1994 | Hollingsworth |
| 5,374,773 A | 12/1994 | Hollingsworth |

OTHER PUBLICATIONS

Berman, A., et al., Science, 269:515–518 (1995).
Chance, R.R., et al., J. Chem. Phys. 71:206–211 (1979).
Charych, D.H., et al., Science, 261:585–588 (1993).
Crooks, R.M., et al., Acc. Chem. Res. 31:219–227 (1998).
Deckert, A.A., et al., Langmuir, 10:1948–1954 (1994).
Huang, G., et al., Tetrahedron 54:1355–1360 (1998).
Huggins, K.E., et al., Macromolecules, 30:5305–5312 (1997).
Jung, S., et al., J. Comp. Chem. 17:238–249 (1996).
Jung, S., et al., J. Lipid Res. 35:1057–1065 (1994).
Leaver, J., et al., Biochem. Biophys. Acta 727:327–334 (1983).
Lee, J., et al., J. Am. Chem. Soc., 120:5855–5863 (1998).
Lio, A. et al., Langmuir 13:6524–6532 (1997).
Lovell, P.A., et al., Macromolecules 31:842–849 (1998).
Mayer, E.S., et al., J. Chem. Engin. Data 31:272–274 (1986).
Mino, N., et al., Langmuir 8:594–598 (1992).
Mowery, M.D., et al., Phys. Chem. B. 101:8513–8519 (1997).
Nallicheri, R.A., et al., Macromolecules 24:517–525 (1991).
Nava, et al., Macromolecules 23:3055–3063 (1990).
Okada, S., et al., Acc. Chem. Res. 31:229–239 (1998).
Reichert, A., et al., J. Am. Chem. Soc. 117:829–830 (1995).
Rubner, M.F., et al., 20:1296–1300 (1987).
Saito, A., et al., Langmuir, 12:3938–3944 (1996).
Salem, L., Can. J. of Biochem. and Physiol. 40:1287–1298 (1962).
Spevak, W., et al., J. Am. Chem. Soc. 115:1146–1147 (1993).
Uchikawa et al., Bull, Chem. Soc. Jpn. 61:2025–2029 (1988).
Wenzel, M., et al., J. Am. Chem. Soc. 111:6123–6127 (1989).
Werkman, P.J., et al., Langmuir 14:157–164 (1998).

*Primary Examiner*—David W. Wu
*Assistant Examiner*—Tanya Zalukaeva
(74) *Attorney, Agent, or Firm*—Ian C. McLeod

(57) ABSTRACT

Polyacetylene compounds and process for the preparation thereof from a chiral dihydroxy amide are described. The compounds preferably have diacyl groups attached to the amide. The compounds are useful for making films which are electrically conductive, near infrared absorbing, polarizing, and have the optical characteristic and other properties of polyacetylenes.

5 Claims, 12 Drawing Sheets

ORDERED POLYACETYLENES AND PROCESS FOR THE PREPARATION THEREOF

CROSS-REFERENCE TO RELATED APPLICATION

This application is a divisional application Ser. No. 09/273,219 filed on Mar. 19, 1999 now U.S. Pat. No. 6,194,529.

STATEMENT REGARDING FEDERALLY SPONSORED RESEARCH OR DEVELOPMENT

This invention was supported by National Science Foundation Grant Number IBN 9507189. The U.S. government has certain rights in this invention.

BACKGROUND OF THE INVENTION (1) Field of the Invention

The present invention relates to novel ordered polyacetylene compounds with side-by-side carbon chains and aligned acetylene groups in each chain and to a process for the preparation thereof. In particular, the present invention preferably relates to polydiacetylene compounds with two adjacent acetylene groups in each chain.

(2) Description of Related Art

Diacetylenes polymerize to give systems with electrical and optical properties that can potentially be exploited for a variety of important applications. These include conductive devices, electrochromic devices and biosensors. In order for polymerization to be possible, the double bonds must be aligned in very close proximity and with the correct geometry. It is also necessary for several of these chains to be so aligned. The problem of ordering these systems to give layers with uniform properties is a difficult one and current approaches involve the use of Langmuir-Blodgett troughs and thiol-metal anchors. The design and synthesis of diacetylene molecules that can self-assemble to form stable, uniform 2-dimensional systems are important areas of endeavor.

There is an increasing amount of interest in the design of planar lamellar systems containing conjugated polydiacetylene functions. These systems are known to display several interesting properties that could lend themselves to the fabrication of a variety of devices (Okada, S., et al., Acc. Chem. Res. 31:229–239 (1998); and Crooks, R. M., et al., Acc. Chem. Res. 31:219–227 (1998)). For instance, they display mechano-optical effects in which compressing the polydiacetylene layers lead to a change in color of the films (Nallicheri, R. A., et al., Macromolecules 24:517–525 (1991); and Lovell, P. A., et al., Macromolecules 31:842–849 (1998)). In other experiments, attaching a carbohydrate molecule to a polydiacetylene layer resulted in a change in color when viral particles bound to the carbohydrate (Reichert, A., et al., J. Am. Chem. Soc. 117:829–830 (1995); and Spevak, W., et al., J. Am. Chem. Soc. 115:1146–1147 (1993)). Polydiacetylene layers also demonstrate color changes in response to alterations in temperature (Chance, R. R., et al., J. Chem. Phys. 71:206–211 (1979); Rubner, M. F., et al., 20:1296–1300 (1987); and Wenzel, M., et al., J. Am. Chem. Soc. 111:6123–6127 (1989)), pH (Mino, N., et al., Langmuir 8:594–598 (1992)) and on exposure to some solvents (Nava, A. D., et al., Macromolecules 23:3055–3063 (1990)). Polyacetylene is well recognized for its high electrical conductivity. Unfortunately, it forms fibers not films, and its high insolubility and general physical intractability makes it unsuitable for many applications especially when lamellar systems are desirable. Under favorable circumstances, the use of amphophilic molecules with acetylene groups in the hydrocarbon chains leads to film formation (Lio, A., et al., Langmuir 13:6524–6432 (1997) and Werkman, P. J., et al., Langmuir 14:157–164 (1998)). However, such molecules often contain only one hydrocarbon chain and they have a tendency to form micellar systems. In order to obtain suitable films, the chains then either have to be anchored to surfaces, or Langmuir-Blodget troughs have to be employed (Charych, D. H., et al., Science 261:585–588 (1993); Berman, A., et al., Science, 269:515–518 (1995); Saito, A., et al., Langmuir, 12:3938–3944 91996); Deckert, A. A., et al., Langmuir, 10:1948–1954 (1994); and Mowery, M. D., et al., Phys. Chem. B, 101:8513–8519 (1997)). One serious problem with the ordering of actylenic thiols on gold and other metal surfaces is the difficulty in ensuring that the chains are aligned so that the alkyne groups are in a proper orientation and close enough to allow the polymerization process. This is difficult because imperfections on the metal surface of only a few atoms in dimension force adjacent chains to be at different heights, thus separating the acetylenic groups by too great a distance. A substrate-independent way of ordering alkyl chains with diacetylenic functions is therefore highly desirable. Molecular self-assembly has much promise in this area.

Phospholipids readily form stable lamellar systems. The inclusion of conjugated diacetylenic groups at the same position in each acyl chain of a phospholipid chain (FIG. 2) should give ideal self-assembling units which can be polymerized to form highly organized, stable, 2-dimensional systems containing a conducting polydiacetylene layer. Unfortunately, the synthesis of phospholipids is extremely laborious. One approach that has been tried is to use microorganisms to carry out the integration of fatty acids containing diacetylenic functions into phospholipids. Using this strategy as much as 90% integration of diacetylenic fatty acids into microbial phospholipids was obtained (Leaver, J., et al., Biochim. Biophys. Acta 727:327–334 91983)). There are some problems with this approach however; because the membrane is only two molecules thick and just surrounds the cell, the actual amount of material recovered per gram of cell mass is extremely small. In addition to this, the lipid species made by any one microorganism are extremely diverse and may include neutral, and negatively charged headgroups with different structures. It is a challenge to separate species with only one type of headgroup and, even then, there is a tremendous amount of diversity in the fatty acid species that are derived from the normal microbial metabolism. Another disadvantage stems from the fact that microorganisms contain a myriad of membrane-associated enzymatic activities that can reduce or oxidize the diacetylenic functions. Because the microorganisms make fatty acids de novo, it is very unlikely that any living system exists that will incorporate only foreign fatty acids into its membrane lipids.

Therefore, it is clear that only synthetic approaches have the potential for producing pure phospholipids or phospholipid analogs containing diacetylenic functions in the fatty acyl chains and which have a high degree of chemical integrity. Because of the difficulty in preparing phospholipids, simpler analogs which still contain the critical structural elements of phospholipids, a chiral 1,2-diacyl moiety and a polar headgroup, are desirable. Even more desirable are phospholipid analogs that have the general structure of the lipids found in bacteria that inhabit environments with extremely high temperatures or extremes of pH. The lipids of such organisms contain two transmembrane hydrocarbon chains that are linked to a headgroup at either end. In some bacteria the linkages are ether linkages but in others (Lee, J., et al., J. Am. Chem. Soc., 120:5855–5863 (1998); Jung, S., et al., J. Lipid Res. 35:1057–1065 (1994)), they are ester functions (FIG. 2). Such molecules should self-assemble to form extremely stable lamellar systems without the aid of devices such as Langmuir-Blodgett troughs. They would be excellent targets for the preparation of planar polydiacetylenic systems.

Objects

It is therefore an object of the present invention to provide novel polyacetylene compounds and a process for the preparation thereof. It is further an object of the present invention to provide novel polydiacetylene compounds which have unique properties. Further still, it is an object of the present invention to provide a process which produces the polyacetylenic compounds economically and in high purity. These and other objects will become increasingly apparent by reference to the following description and the drawings.

SUMMARY OF THE INVENTION

The present invention relates to a process for producing an ordered polyacetylene compound with two side-by-side carbon chains and aligned acetylene groups in each side chain. The process comprises reacting a 1-N,N-dialkylaminoalkyl-3,4-dihydroxyalkyl amide with an acetylene containing acyl halide in a reaction mixture to produce 1-N,N-dialkyamino-3,4-di(acetylenoxy group) alkylamide as the ordered polyacetylene compound. In particular, the present invention relates to a process for producing an ordered polydiacetylene compound with two side-by-side carbon chains and aligned diacetylene groups in each side chain.

The present invention also relates to an ordered polyacetylene compound with two side-by-side carbon chains and aligned acetylene groups in each chain which comprises 1-N,N-dialkyl amino alkyl-3,4-di(acetyleneoxy group) alkylamide. In particular, the compound is an ordered polydiacetylene compound with two side-by-side carbon chains and aligned diacetylene groups in each chain which comprises 1-N,N-dialkyl amino alkyl-3,4-di(acetyleneoxy group)alkylamide.

The present invention also relates to a film prepared from monomers of the polyacetylene. The film can be as a sheet or deposited on a surface. In the film the acetylene groups line up together across the sheet. In particular the film is prepared from monomers of polydiacetylene. The present invention further relates to a process for preparing the film from monomers of the polyacetylene, or in particular, monomers of the polydiacetylene.

BRIEF DESCRIPTION OF DRAWINGS

FIG. 5A is a section analysis over a 4 $\mu$M length. FIG. 5B is a top view of the same area as in FIG. 5A. FIG. 5C is a perspective surface plot of the same area as in FIG. 5B.

FIG. 6A is a section analysis over a 2 $\mu$M length. FIG. 6B is a top view of the same area as in FIG. 6A. FIG. 6C is a perspective surface plot of the same area as in FIG. 6B.

DETAILED DESCRIPTION OF THE INVENTION

Figure 1A:
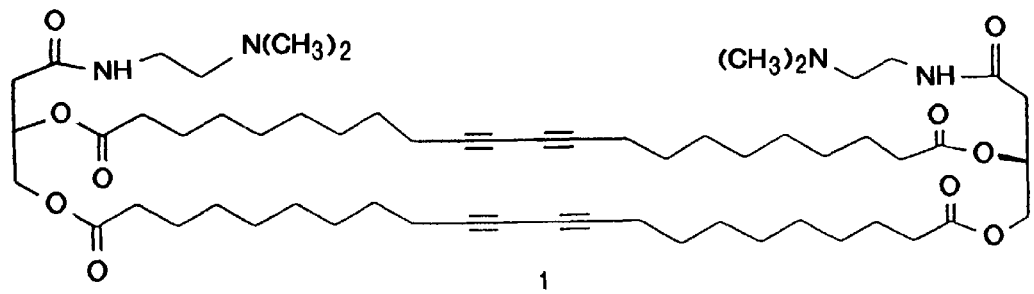
FIGS. 1A, 1B and 1C are drawings showing the structures of compounds 1 and 2 of the present invention and intermediate compound 3.

The present invention relates to a process for producing an ordered polyacetylene compound with two side-by-side carbon chains and aligned acetylene groups in each chain which comprises reacting a 1-N,N-dialkylaminoalkyl-3,4-dihydroxyalkyl amide with an acyl halide in a reaction mixture to produce 1-N,N-dialkylamino-3,4-di(acetyleneoxy group)alkylamide as the ordered polyacetylene compound, wherein alkyl in the dialkyl amino is between 1 to 6 carbon atoms and acetyleneoxy group is between 6 to 50 carbon atoms in a linear alkylene chain with the acetylene groups; and separating the ordered polyacetylene compound from the reaction mixture. In particular, to a process wherein the diacyl dihalide is an acyl halide and the ordered polyacetylene compound has two alkyl amide groups positioned at each of the opposed ends of the acetylene dioxy group.

The present invention further relates to a process for producing an ordered polydiacetylene compound with two side-by-side carbon chains and aligned diacetylene groups in each chain which comprises reacting a 1-N,N-dialkylaminoalkyl-3,4-dihydroxyalkyl amide with an acyl halide in a reaction mixture to produce 1-N,N-dialkylamino-3,4-di(acetyleneoxy group)alkylamide as the ordered polydiacetylene compound, wherein alkyl in the dialkyl amino is between 1 to 6 carbon atoms and acetyleneoxy group is between 6 to 50 carbon atoms in a linear alkylene chain with the diacetylene groups; and separating the ordered polydiacetylene compound from the reaction mixture. In particular, to a process wherein the diacetylene oxyhalide is an diacyl dihalide and the ordered polyacetylene compound has two alkyl amide groups positioned at each of the opposed ends of the diacetylene dioxy group.

In an embodiment further still, the present invention relates to a process for producing an ordered polydiacetylene compound with two side-by-side chains and aligned diacetylene groups in each chain which comprises reacting a single chiral 1-N,N-dimethylaminoethyl-3,4-dihydroxybutramide with an acyl halide in a reaction mixture to produce 1-N, N-dimethyl amino-3,4-di(diacetyleneoxy group)butyramide as the ordered polydiacetylene compound; and separating the ordered polydiacetylene compound from the reaction mixture. In particular to a process wherein the acyl halide is a diacyl dihalide and the ordered polyacetylene has two alkylamide groups positioned at each of the opposed ends of acetylene dioxy group.

The present invention relates to an ordered polyacetylene compound with two side-by-side carbon chains and aligned acetylene groups in each chain which comprises 1-N,N-dialkyl amino alkyl-3,4-di(acetyleneoxy group)alkylamide, wherein alkyl in the dialkyl amino is between 1 to 6 carbon atoms and the acetyleneoxy group contains between 6 to 50 carbon atoms in a linear alkylene chain with the acetylene groups. In particular to the ordered polyacetylene compound wherein the acetyleneoxy group is an acetylene dioxy group and the ordered polyacetylene compound has two alkyl amide groups positioned at each of the opposed ends of the acetylene dioxy group.

The present invention further relates to an ordered polydiacetylene compound with two side-by-side carbon chains and aligned diacetylene groups in each chain which comprises 1-N,N-dialkyl amino alkyl-3,4-di(acetyleneoxy group)alkylamide, wherein alkyl in the dialkyl amino is between 1 to 6 carbon atoms and polyacetylene contains between 6 to 50 carbon atoms in a linear alkylene chain with the acetylene groups. In particular, present invention relates to the ordered polyacetylene compound wherein the acetyleneoxy group is an acetylene dioxy group and the ordered polyacetylene compound has two alkyl amide groups positioned at each of the opposed ends of the acetylene dioxy group.

The present invention relates further still to an ordered polydiacetylene compound which comprises 1-N,N-dimethyl amino ethyl-3,4-di(diacetyleneoxy group) butyramide, wherein the diacetyleneoxy group is two linear alkylene chains with diacetylene groups aligned in each chain. In particular, the present invention relates to the ordered polydiacetylene compound wherein the diacetyleneoxy group is a diacetylene dioxy group and the ordered polyacetylene compound has an alkylamide group positioned at opposed ends of the diacetylene dioxy group.

Figure 1C:
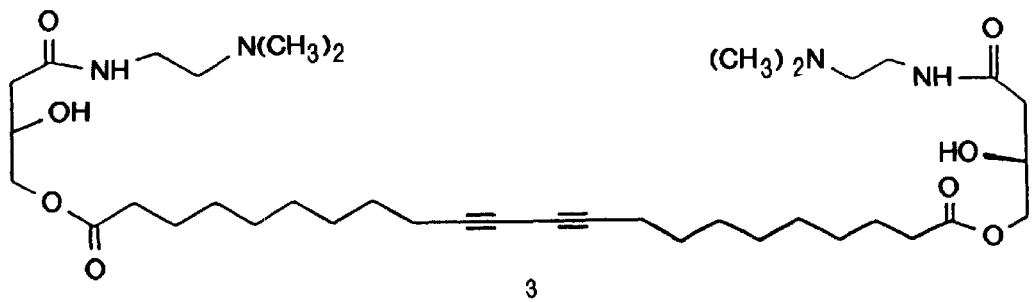
Figure 2:
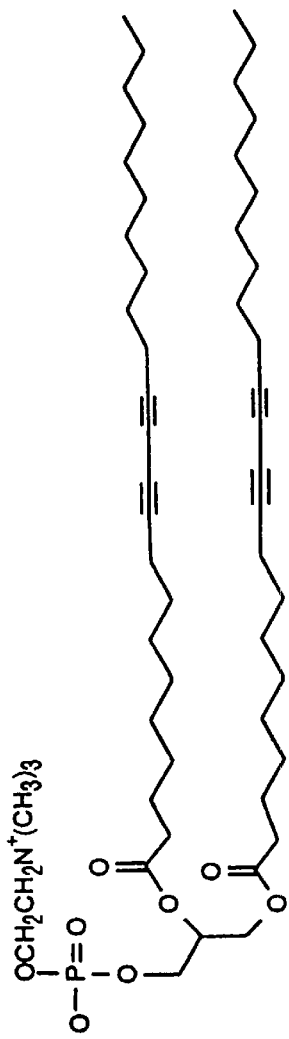
FIG. 2 is a drawing showing the structure of a typical phospholipid (phosphatidyl choline) containing diacetylenic fatty acyl groups known to the prior art.
Figure 3:
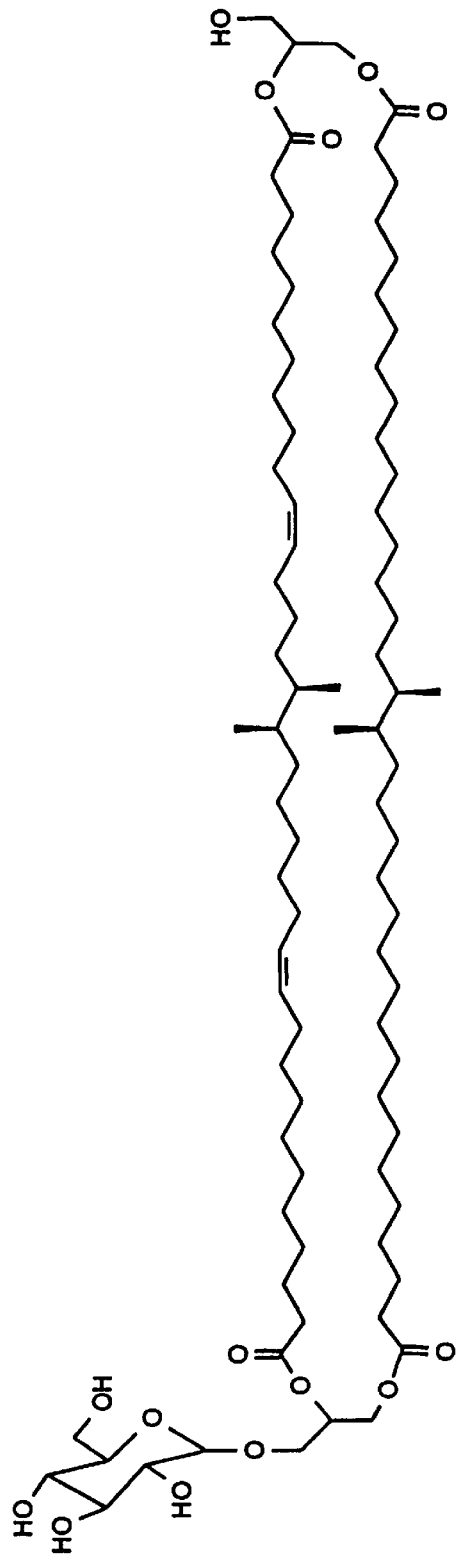
FIG. 3 is a drawing showing the structure of a membrane lipid from a thermotropic bacterium known to the prior art.

In a first embodiment of the present invention the compound has the structure of compound 1 as shown in FIG. 1A. In the first embodiment compound 1 is either (S) chiral or (R) chiral. In a second embodiment, the compound has the structure of compound 2 as shown in FIG. 2A and the compound is either (S) chiral or (R) chiral. In a third embodiment, the compound is compound 3 as shown in FIG. 1C and the compound is either (S) chiral or (R) chiral. Chirality of the polydiacetylene compounds made according to the present invention is a function of whether the preferred 3-hydroxybutyrolactone is (S) chiral or (R) chiral.

The present invention also relates to a film prepared from monomers of the polyacetylene compound. The film can be cast as a sheet or deposited on a surface. In the film, the acetylene groups line up together across the sheet. In a particular embodiment, the film is prepared from the polydiacetylene compound. The present invention further relates to a process for preparing the film from the polyacetylene compound, or in particular, the polydiacetylene compound.

Thus, the present invention relates to a film comprising monomers of ordered polydiacetylene with two side-by-side carbon chains and aligned diacetylene groups in each chain which comprises 1-N,N-dialkyl amino alkyl-3,4-di (acetyleneoxy group)alkylamide, wherein alkyl in the dialkyl amino is between 1 to 6 carbon atoms and acetyleneoxy group contains between 6 to 50 carbon atoms in a linear alkylene chain with the acetylene groups assembled into a two-dimensional polymer structure. In a specific embodiment, the acetyleneoxy group is an acetylene dioxy group and the ordered polyacetylene compound has two alkyl amide groups positioned at each of the opposed ends of the acetylene dioxy group.

The present invention also relates to a process for producing the film of monomers of ordered polydiacetylene with two side-by-side carbon chains and aligned diacetylene groups in each chain which comprises reacting a 1-N,N-dialkylaminoalkyl-3,4-dihydroxyalkyl amide with a diacetyleneoxyhalide in a reaction mixture to produce 1-N,N-dialkylamino-3,4-di(acetyleneoxy group)alkylamide as the ordered polydiacetylene compound, wherein alkyl in the dialkyl amino is between 1 to 6 carbon atoms and acetyleneoxy group is between 6 to 50 carbon atoms in a linear alkylene chain with the diacetylene groups; separating the ordered compound from the reaction mixture; dissolving the compound in a solvent; and depositing the dissolved compound on a substrate to form a two-dimensional structure. In a specific embodiment of the process,, the acyl halide is a diacetylene dihalide and the ordered polyacetylene compound has two alkyl amide groups positioned at each of the opposed ends of the diacetylene dioxy group.

The present invention further relates to a film composed of monomers of ordered polyacetylene with two side-by-side carbon chains and aligned acetylene groups in each chain which comprises 1-N,N-dialkyl amino alkyl-3,4-di (acetyleneoxy group)alkylamide, wherein alkyl in the dialkyl amino is between 1 to 6 carbon atoms and acetyleneoxy group contains between 6 to 50 carbon atoms in a linear alkylene chain with the acetylene groups to assemble a two-dimensional polymer structure. In a specific embodiment, the acetyleneoxy group is an acetylene dioxy group and the ordered polyacetylene compound has two alkyl amide groups positioned at each of the opposed ends of the acetylene dioxy group.

The present invention also relates to a process for producing the film of monomers of ordered polyacetylene with two side-by-side carbon chains and aligned acetylene groups in each chain which comprises reacting a 1-N,N-dialkylaminoalkyl-3,4-dihydroxyalkyl amide with an acyl halide in a reaction mixture to produce 1-N,N-dialkylamino-3,4-di(acetyleneoxy group)alkylamide as the ordered polyacetylene compound, wherein alkyl in the dialkyl amino is between 1 to 6 carbon atoms and acetyleneoxy group is between 6 to 50 carbon atoms in a linear alkylene chain with the acetylene groups; separating the ordered polydiacetylene compound from the reaction mixture; dissolving the compound in a solvent; and depositing the dissolved compound on a substrate to form the two-dimensional polymer structure.

The present invention further relates to a film of monomers of ordered polydiacetylene which comprises 1-N,N- dimethyl amino ethyl-3,4-di(diacetyleneoxy group) butyramide, wherein diacetyleneoxy is two linear alkylene chains with diacetylene groups aligned in each chain assembled into a two-dimensional polymer structure. In one embodiment of the invention, the diacetyleneoxy group is a diacetylene dioxy group and the ordered polyalkylene compound has an alkylamide group positioned at opposed ends of the diacetylene dioxy group. In a specific embodiment of the invention, the acyl halide is an acyl dihalide and the ordered polyacetylene compound has two alkyl amide groups positioned at each of the opposed ends of the acetylene dioxy group.

Finally, the present invention relates to a process for producing a film of monomers of ordered polydiacetylene with two side-by-side chains and aligned diacetylene groups in each chain which comprises reacting a single chiral 1-N,N-dimethylaminoethyl-3,4-dihydroxybutramide with an acyl halide in a reaction mixture to produce 1-N,N-dimethyl amino-3,4-di(diacetyleneoxy group)butyramide as the ordered polydiacetylene compound; separating the ordered polydiacetylene compound from the reaction mixture; dissolving the compound in a solvent; and depositing the dissolved compound on a substrate to form a two-dimensional structure. In a particular embodiment, the diacetylene oxyhalide is a diacetylene dioxy halide and the ordered polyacetylene has two alkylamide groups positioned at each of the opposed ends of acetylene dioxy group.

In a first embodiment of a film of the present invention the monomer comprising the film has the structure of compound 1 as shown in FIG. 1A. In the first embodiment, the monomer is compound 1 which is either (S) chiral or (R) chiral. In a second embodiment, the monomer has the structure of compound 2 as shown in FIG. 2A and the monomer is either (S) chiral or (R) chiral. In a third embodiment, the monomer is compound 3 as shown in FIG. 1C and the monomer is (S) chiral or (R) chiral. Chirality of the polydiacetylene monomers made according to the present invention is a function of whether the preferred 3-hydroxybutyrolactone is (S) chiral or (R) chiral.

Preparation of polyacetylenes according to the present invention requires a gamma-lactone (3-hydroxybutyrolactone), a reactant amide, and a reactant acetylene oxyhalide. The reactant amide can have the formula:

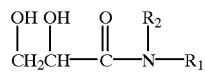

where $R_1$ and/or $R_2$ is a dialkyl aminoalkyl group, di-t-butyldicarbonate, formyl, acetyl or other blocking group. Preferred is the dimethylaminoethylene group in the intermediate compound 5 in FIG. 10 where $R_1$ or $R_2$ is hydrogen.

Figure 10:
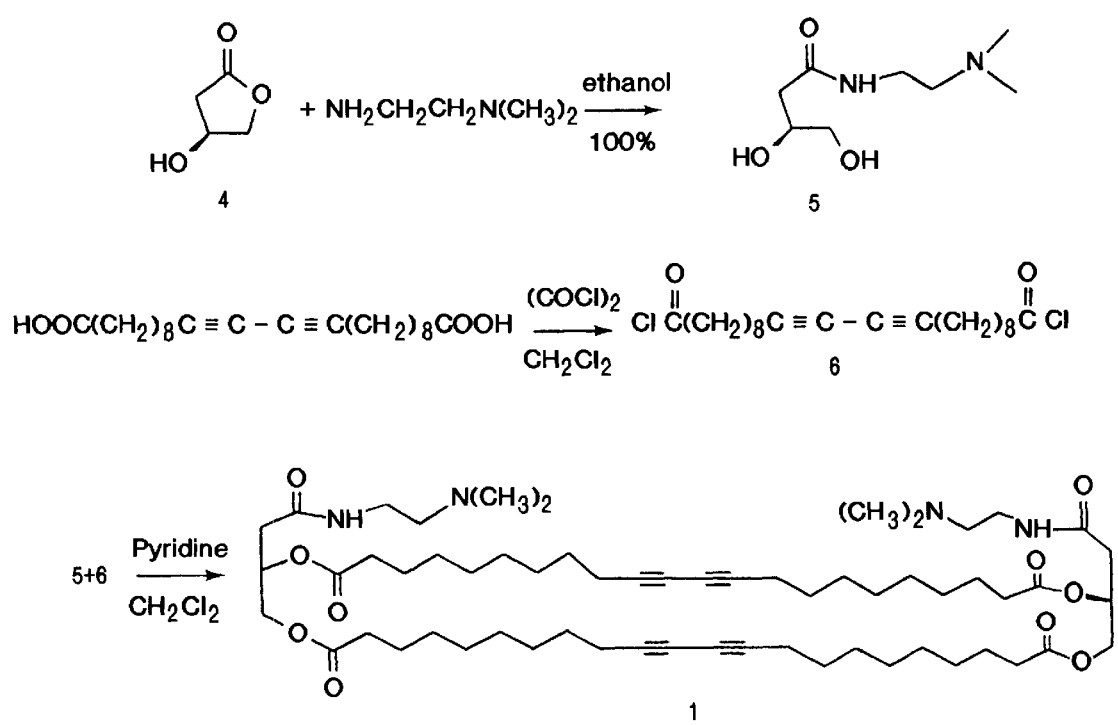
FIG. 10 is a drawing showing the synthesis of compound 1.

The reactant acyl halide can have the formula:

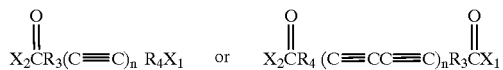

wherein in n is 1 or 2, wherein at least one of $R_3$ or $R_4$ has a group comprising $(CH_2)_n$, $(CH=CH)_n$, $(C\equiv C)_n$, and $(C=O)_{0-1}$ wherein n is equal to or greater than 0, and wherein $X_1$ and/or $X_2$ which is reactive with the hydroxyl groups of the amide and the other group $X_1$ or $X_2$ a non-reactive group or a reactive second group. FIG. 10 shows the product compound 1 where $X_1$ and $X_2$ are chloride, so that a base can condense the hydroxyls of the amide with the chloride of the acetylene compound 6 by removing hydrogen chloride. The acyl halide is prepared from the corresponding acid reacted with an oxyacyl halide.

Typically the base is a Lewis base amine such as pyridine which reacts with the hydrogen chloride in a non-polar solvent, particularly a halogenated solvent such as methylene dichloride.

Figure 1B:
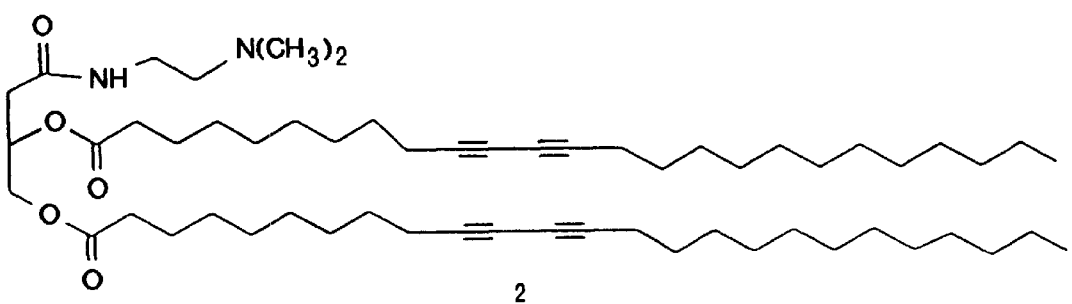

The proper alignment of acyl chains can be obtained by the synthesis of compounds 1 and 2 (FIG. 1). Like typical phospholipids, they have two long acyl chains preferably attached to a chiral 1,2-diol. They also have a dimethylaminoethane head blocking group. An important feature the two compounds have is that they are preferably chiral. When the diacetylenic units polymerize, chiral two dimensional polymers will be obtained. The synthesis of (S)-3-Hydroxy-γ-butyrolactone which was the source of the chirality for compounds 1 and 2 has been described earlier in U.S. Pat. Nos. 5,374,773, 5,319,110, and 5,292,939 to Hollingsworth which are herein incorporated by reference. The synthetic routes are outlined in FIGS. 10 and 11, respectively. Compounds 1 and 2 are new compositions of matter.

Figure 11:
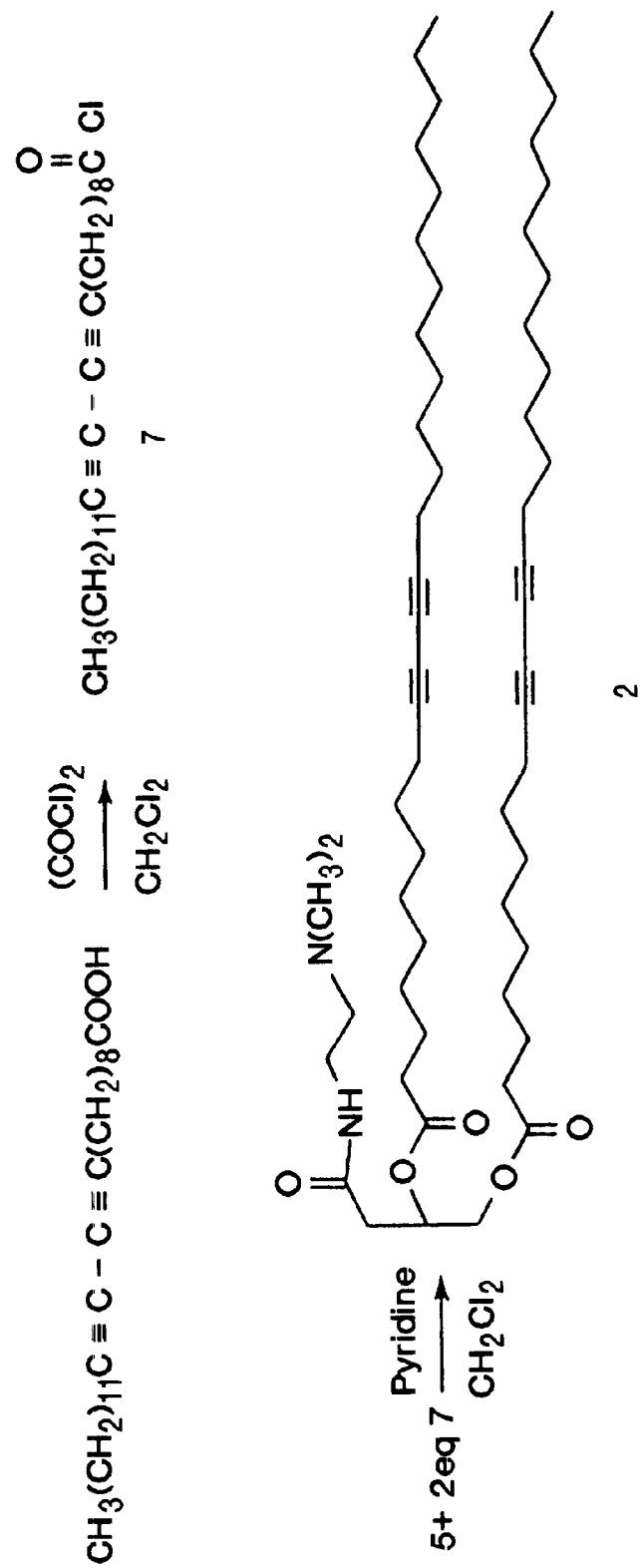
FIG. 11 is a drawing showing the synthesis of compound 2.

Preparation of Compounds 1 and 2. The chiral, diacetylenic compounds 1 and 2 were obtained in very good yield. In the case of 2 the preparation necessitated only three steps all of which proceeded in good yield. To prepare either compound 1 or 2 (Examples 2 and 3, respectively), only three steps were necessary, all of which proceeded in good yield. The first step shown in Example 1 was reacting (S)-3-hydroxybutyrolactone (compound 4) with N,N-dimethylaminoethyl to produce the N,N-dimethylaminoethyl-3,4-dihydroxybutyramide (compound 5). The step to form compound 5 is essentially quantitative (FIG. 10). The second step was to make acetylene dioxyhalide compound 6 (FIG. 10) or acetylene oxyhalide compound 7 (FIG. 11). This step is performed by reacting an acetyleneoxy with an oxalyl halide such as $COCl_2$ in an anhydrous solvent such as dichloromethane. Finally, in the third step a compound 5 is with either compound 6 or 7 in a condensation reaction to make compound 1 or 2, respectively.

In the case of compound 1, the only possible complication was the formation of the isomeric structures in which the acyl chain was linked to the primary hydroxyl group on one side and to the secondary group on the other. This did not occur since only the intermediate compound 3 (FIG. 1) in which a single chain was linked to the primary position of an N-alkyl dihydroxybutyramide on each side was detected under conditions in which the reaction was only partially complete. The identity of the intermediate species as compound 3 was readily determined by $^1$H-NMR and $^{14}$C-NMR spectroscopy. The signals for the methylene protons attached to oxygen appears at 4.30 and 4.10 ppm substantially downfield from their original positions in the starting diol. The methine proton signal was not shifted from 4.06 ppm. There were no signals corresponding to un-esterified primary alcohols in the spectrum although a substantial degree of under-esterification of the secondary position was evident from the spectra of the total mixture.

Figure 4:
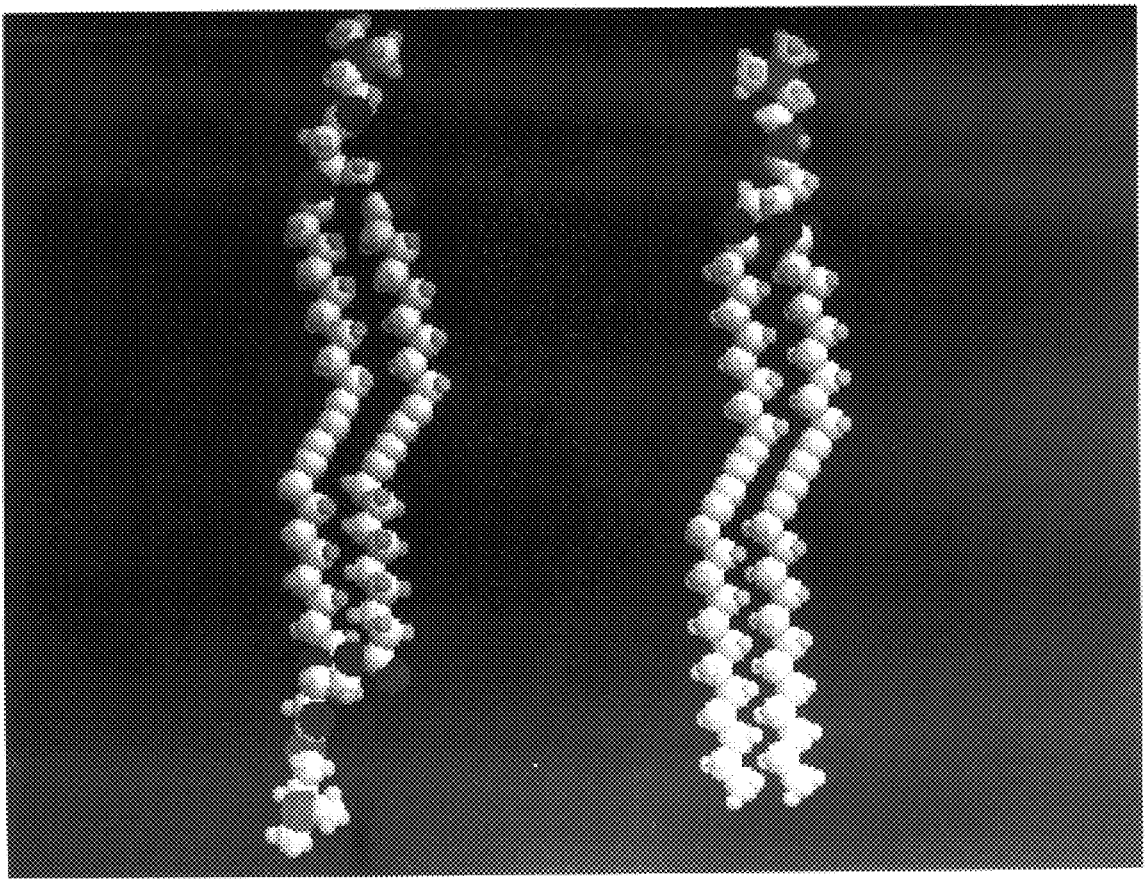
FIG. 4 is a schematic drawing showing space filling models having the conformations of compounds 1 (left) and 2 (right) as indicated by NMR spectroscopy and molecular mechanics calculation. Black is oxygen or nitrogen. Small grey dots are hydrogen and large grey dots are carbon.

Supramolecular structure, Stability, and Long-Range Order. The supramolecular structures of compounds 1 and 2 were determined by NMR spectroscopy (Examples 2 and 3, respectively). The parallel orientation of the two acyl chains of both compounds 1 and 2 was quite evident by NMR spectroscopy from the coupling constants of the methylene protons attached to the acyloxy group. The coupling constants between these protons and the neighboring methine proton are indicative of the relative orientation of the acyloxy groups on these two carbons. The splittings were similar to those observed in a similar molecule where the acyl chains bore pyrenyl substituents at their termini and were known to be parallel by virtue of the fact that the pyrenyl groups displayed excimer emission (Huang, G., et al., Tetrahedron 54:1355–1360 (1998)). For compound 2, the signals for these methylene protons were two mutually coupled doublet of doublets. One appeared at 4.30 ppm (3.6 Hz and 12.0 Hz) and the other at 4.12 ppm (5.8 Hz and 12 Hz). These values were also similar to those observed for the coupling constants for the 1 and 1' protons with the 2-proton of the glyceryl moiety of diacyl glycerols. Similar results were observed for compound 1 although the signals were considerably broadened in this case because of slower rotational averaging in this latter system. The parallel nature of the acyl chains was also confirmed by X-ray diffraction analysis of the lipid systems in a water/alcohol system (Example 7). Reflections at 4.0 Angstroms in the case of compound 2 and 3.4 Angstroms in the case of compound 1 were observed. These correspond to alkyl chain separations and the smaller value of compound 1 was expected because in this molecule, the chains are held together at both ends. These results in conjunction with molecular mechanics calculations supported the conformation of the molecules as shown in FIG. 4.

The long-range order of the 2-dimensional systems formed by compounds 1 and 2 was examined by a combination of atomic force microscopy (AFM) and laser scanning confocal microscopy using phase-contrast, dark field and polarizing optics (Examples 5 and 6, respectively). As was mentioned earlier, X-ray analysis of the fully hydrated systems indicated that the hydrocarbon chains were arranged in a stacked parallel order as is expected in lamellar systems. A reflection at 60 angstroms corresponding to slightly less than twice the width of a monolayer as measured from the molecular models was observed. This indicated that compound 2 formed slightly interdigitated bilayers. Atomic force micrographs (FIGS. 5A to 5C and 6A to 6C) of layers of compounds 1 and 2 respectively prepared on mica plates demonstrated they formed flat films with a surface variation of only 9.85 nm over a distance of 1331 nm (0.7%) for compound 1, and 12 nm over a 512 nm range (2.3%) for layer compound 2.

Figure 7A:
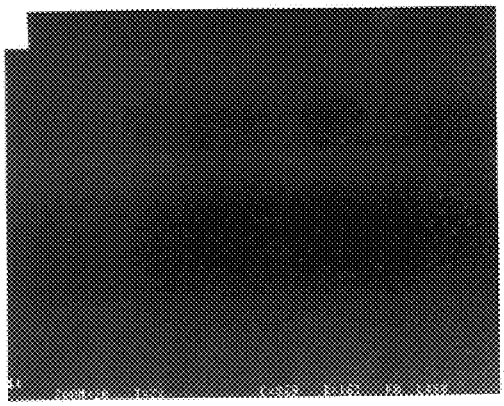
FIGS. 7A, 7B, 7C and 7D are laser scanning confocal micrographs of hydrated films of compound 1 (7A) and compound 2 (7C). The images on the left (FIGS. 7A, 7C) were acquired using cross polarizers and the images to the right (FIGS. 7B and 7D) were obtained using dark field optics. The films are the areas to the right of the fields.
Figure 7B:
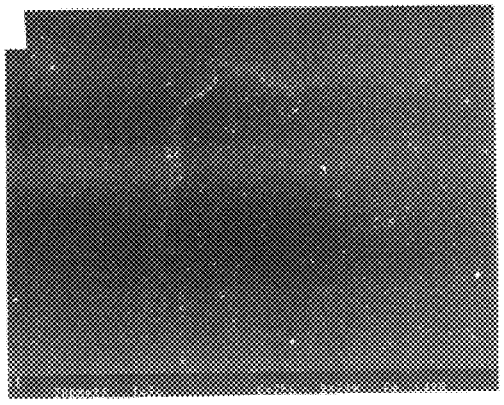
Figure 7C:
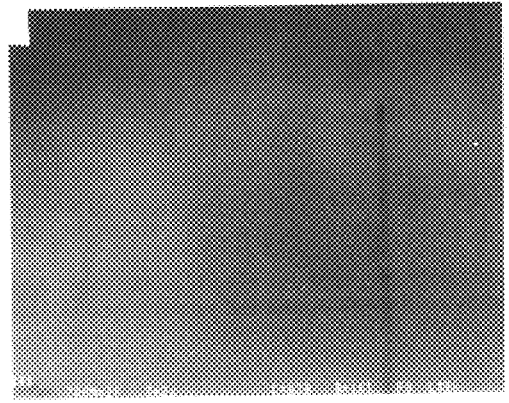
Figure 7D:
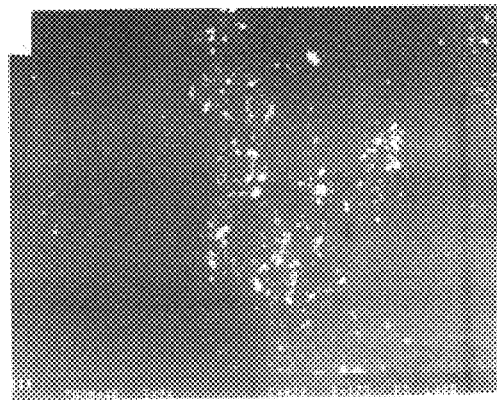

Information on the order and supramolecular organization of the two systems was also obtained by analyzing images obtained from optical laser scanning confocal microscopy. The most useful information was obtained from images using polarizing optics. When using polarizing optics, if the film layers are ordered relative to the plane of the slide and the polarized laser light is blocked by a cross polarizer after going through the layer then only a black background is observed. However, if there are regions of disorder in the film, domains within the layer where the molecules are oriented differently or the layers buckle, then the plane of polarization of the laser light is rotated and is no longer canceled by the cross-polarizing filter. Areas of brightness are then observed in these defective regions. As can be seen in FIGS. 7A and 7C for 1 and 2 respectively, the polarized light micrographs from both systems indicated a very high degree of order with only a few point defects. The phase contrast images are shown in FIGS. 7B and 7D. Significant defects were only observed at the edge of the layers where there was a discontinuity or curvature as the film bent to contact the glass.

Figure 8A:
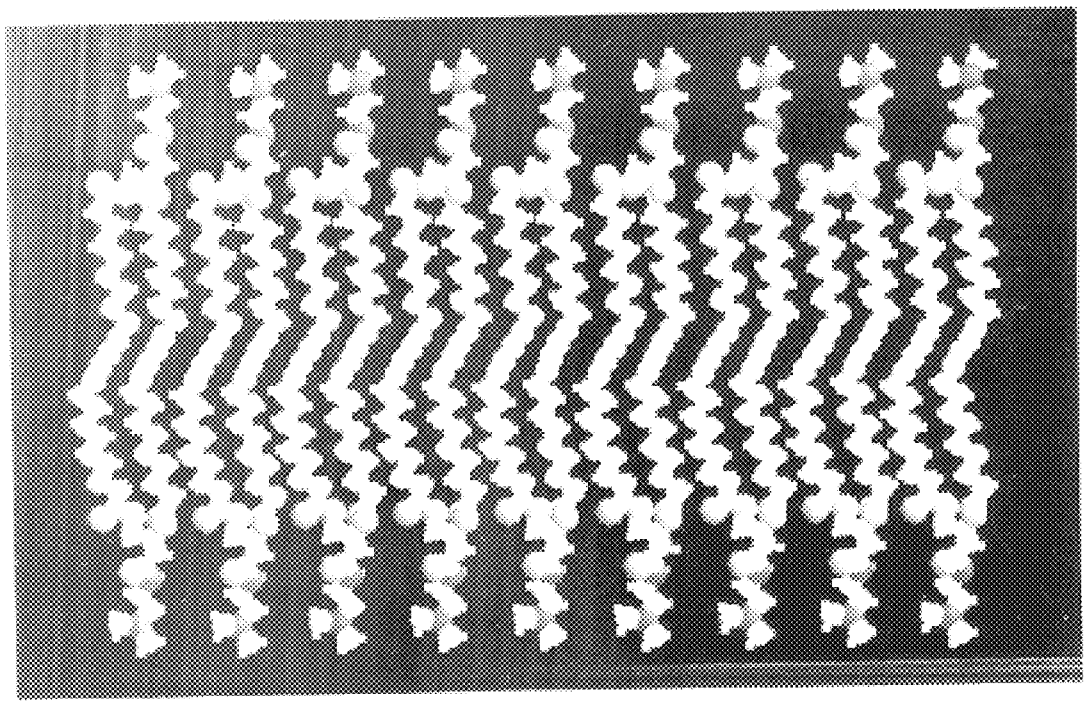
FIGS. 8A and 8B are schematic drawings showing proposed packing models from compound 1 (FIG. 8A) and 2 (FIG. 8B) based on X-ray powder diffraction information and molecular modeling.
Figure 8B:
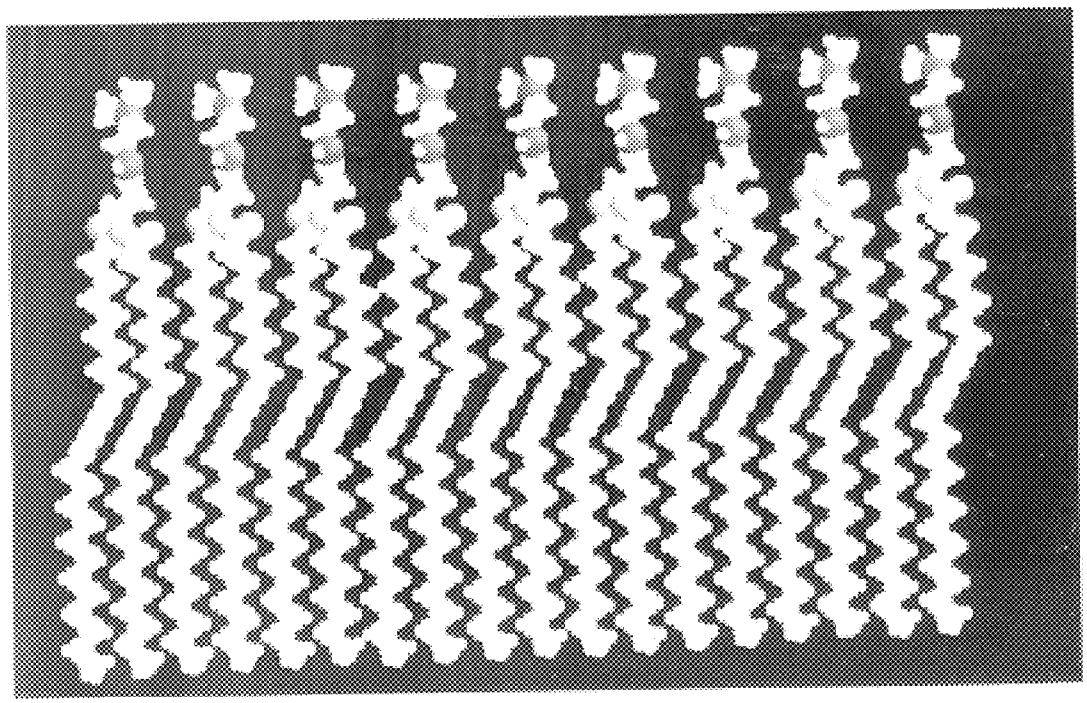
Figure 9A:
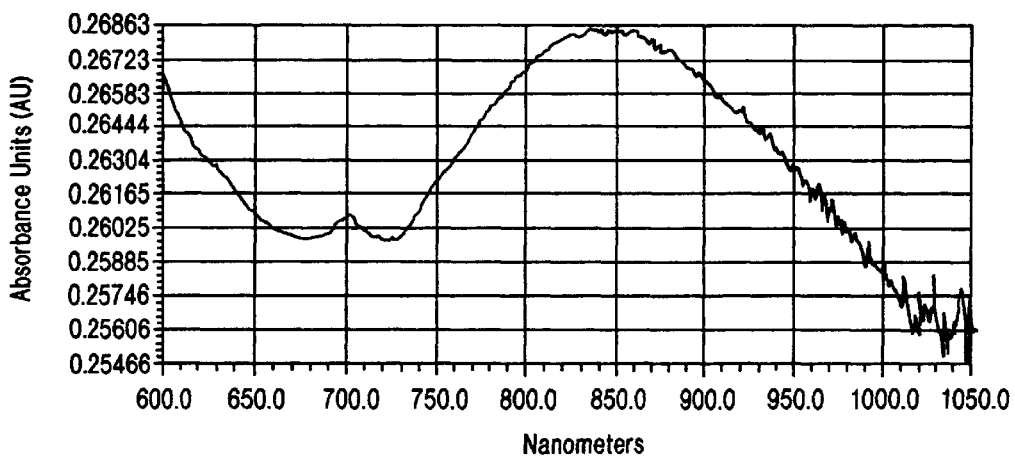
FIGS. 9A to 9H are near infrared spectra of films formed from compound 1 (FIGS. 9A to 9D) and compound 2(FIGS. 9E to 9H). In A, B, E, F, the films were polymerized by UV irradiation and in C, D, G, H, the films were iodine doped. Spectra on the left were acquired in the range of 600–1050 nm, and those to the right were acquired between 880 and 1700 nm.
Figure 9B:
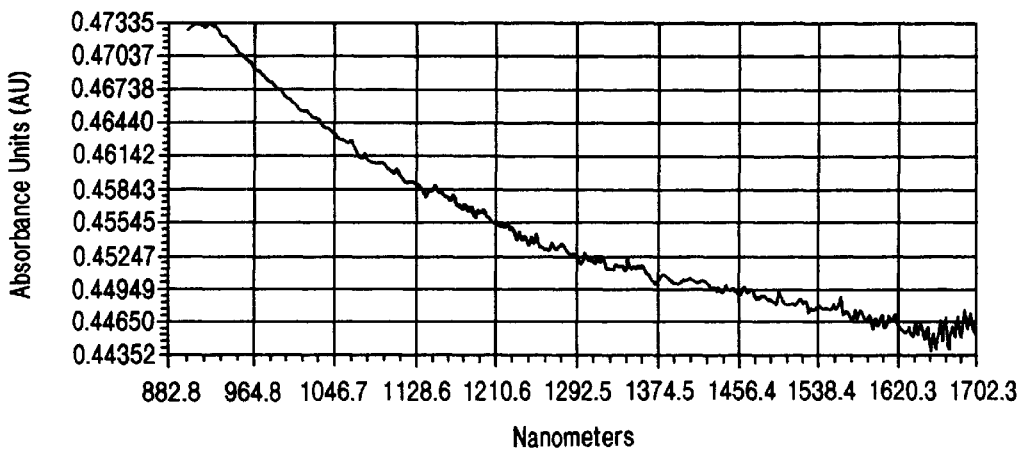
Figure 9C:
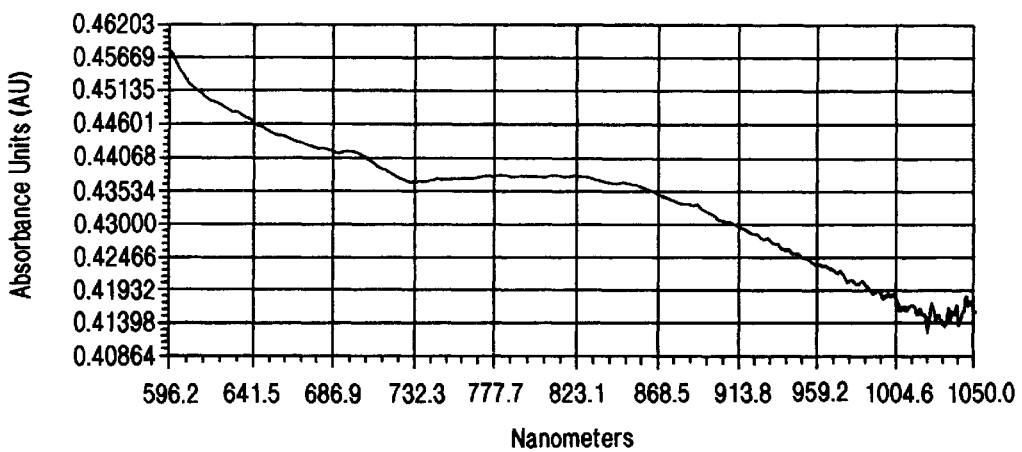
Figure 9D:
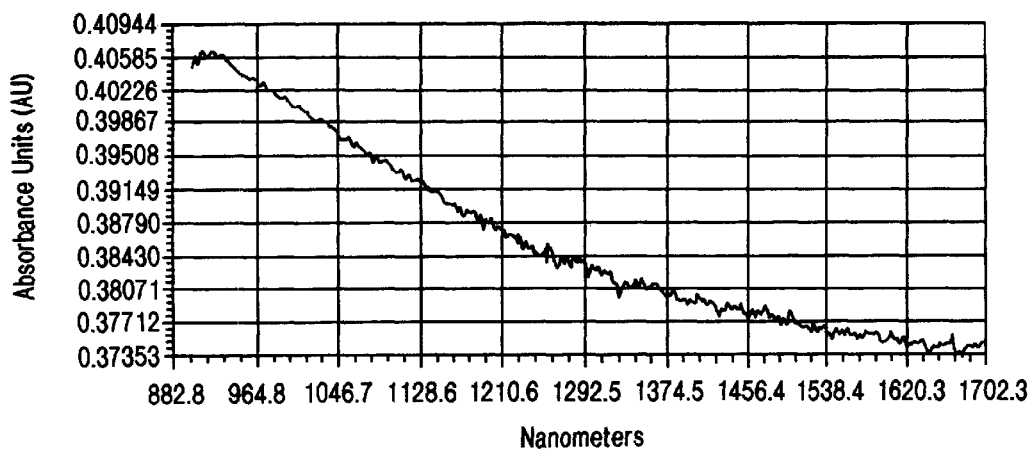
Figure 9E:
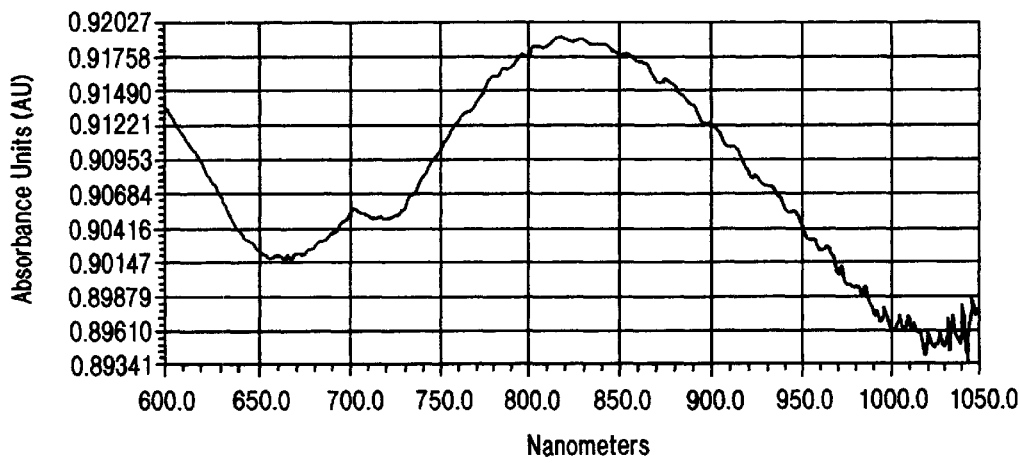
Figure 9F:
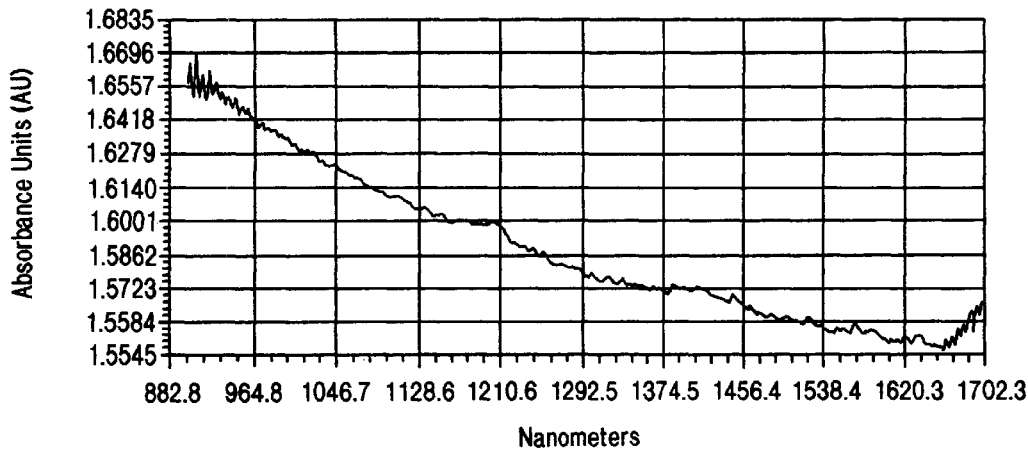
Figure 9G:
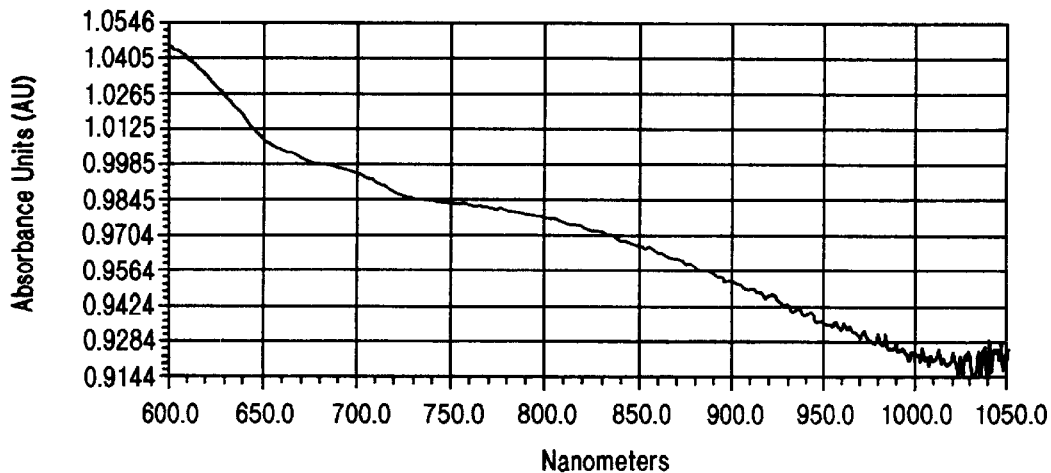
Figure 9H:
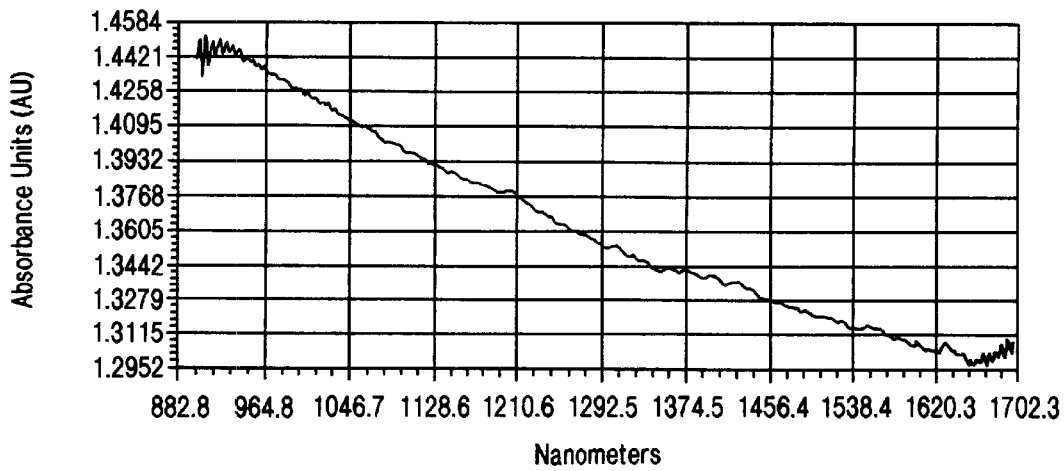

Based on the 3-dimensional film structures proposed for compounds 1 and 2, a packing model which is consistent with their long-range stability and high packing densities of these systems was derived. The model was one that maximized the contact between the hydrocarbon chains such that the $\pi$-interaction was maximized and the alkane chains were in contact along their entire length (FIGS. 8A and 8B). The $\pi$-overlap is expected to be one of the dominant forces between the chains of these molecules. Based on the enthalpies of vaporization of a series of alkanes and conjugated and unconjugated diacetylenes (CRC Handbook of Physics and Chemistry, CRC Press Boca Raton, Fla., U.S.A. (1997); and Mayer, E. S., et al., J. Chem. Engin. Data 31:272–274 (1986)), this component was estimated to be 5.1 Kcals per mole for chains just at the point of separating into the gas phase. This is a lower limit and a much higher value is expected for closely packed chains. The dispersion forces between methylene groups in hydrocarbons is an area that has obtained much attention of special importance has been the problem of calculating the dispersion energy between extended hydrocarbon chains in isolated molecules and large extended arrays (Salem, L., Can. J. of Biochem. and Physiol. 40:1287–1298 (1962); and Jung, S., et al., J. Comp. Chem. 17:238–249 (1996)). In the case of compound 1 where there are 16 methylene groups in contact and the chains are separated by 3.42 Angstroms (based on the X-ray data) the total interaction energy is 45.2 Kcals per mole. In the case of compound 2 where there are 20 methylene groups in contact, but at a greater separation, this energy is expected to be 31.5 Kcals per mole. This gives a lower limit for overall inter-chain interaction energies for compounds 1 and 2 of 50.3 and 36.6 Kcals per mole, respectively. These values are substantially higher than the interaction energies of lipid molecules in biomembranes of comparable acyl chain length. In the case of compound 1, since the hydrocarbon chains are tethered at both ends, the average inter-chain separation is even less. The attraction between the hydrocarbon chains in this case is even greater since it is known to increase by two fold if the two chains move one Angstrom closer from a distance of 5 Angstroms (Salem L., Can. J. of Biochem. and Physiol. 40:1287–1298 (1962)). This dramatic increase in van der Waals energy with reduced chain separation will also be true for the $\pi$-stacking component which is likely to be severely underestimated here.

Formation, Characterization, and Properties of Polydiacetylene Films. Two methods were used to prepare materials with the desired optical and spectroscopic properties that are characteristic of conductive polydiacetylene layers. Such conductive polydiacetylenic systems exhibit intense electronic transitions at long wavelengths. These electronic transitions go beyond the visible spectrum and well into the infrared region. The optical properties of the polydiacetylenic systems made according to the present invention were characterized by near IR spectroscopy experiments. The polydiacetylenic samples were prepared as described in the Examples 2 and 3 and films prepared as in Example 4. IR spectra were measured over two ranges, from 600–1050 ηm and 900–1700 ηm. The results shown in FIGS. 9A to 9H show that the optical behavior of the two compounds polymerized by the same method are similar. Both formed blue films on exposure to UV radiation. In the case of compound 1, there was a strong absorption at 848.3 nm, and this extended to 1700 nm. The maximum for UV-irradiated compound 2 appeared at 817.8 nm. Both spectra displayed a small maximum at ~700 nm. These polymerized blue films turned red on exposure to solvents such as chloroform. Films that were treated with iodine, were bright orange. The absorption maximum for iodine doped compound 1 appeared at 823.1 nm and the maximum for compound 2 was at 772.8 nm. Again there was a small maximum at ~700 nm in both spectra. The occurrence of such intense maxima in the region of 800 nm and beyond with significant absorbance over 1600 nm in the films that were prepared by this method is very unique. It is indicative of the extent of polymerization and demonstrates an exceptionally high long-range order. Typically, no significant absorbance beyond 600–680 nm is observed in these systems (Okada, S., et al., Acc. Chem. Res. 31:229–239 (1998); Charych, D. H., et al., Science, 261:585–588 (1993); Saito, A., et al., Langmuir, 12:3938–3944 (1996); and Huggins, K. E., et al., Macromolecules, 30:5305–5312 (1997)).

Preparation of gamma-lactone. An important precursor for preparing polyacetylenes such as compound 1 or compound 2 is gamma-lactone (compound 4). Methods for making (S) 3,4-dihydroxybutanoic acid and compound 4 therefrom by acidification with mineral oil can be found in U.S. Pat. Nos. 5,319,110, 5,374,773 and 5,292,939 to R. Hollingsworth which are herein incorporated by reference. U.S. Pat. Nos. 4,994,597 and 5,087,751 to Inoue et al which also describes methods for making (S) 3,4-dihydroxybutanoic acid are also hereby incorporated by reference.

An important feature of the present invention is that the synthesis process can produce either pure (R) or (S) chiral polyacetylene compounds. The chirality of the polyacetylene compounds that are synthesized is dependent on whether compound 4 is (R) or (S). Compound 4 can be readily obtained from (R) or (S) 3,4-dihydroxybutanoic acid by acidification with mineral acid, and 3,4-dihydroxybutanoic acid can be readily obtained by oxidation of sugars. The preparation of (S) isomers of 3,4-dihydroxybutanoic acid has been described in U.S. Pat. Nos. 4,994,597, 5,087,751, 5,319,110, 5,292,939 and 5,374,773. Preparation of (R) isomers of gamma-lactone from (R) malic acid has been described by Uchikawa et al., Bull. Chem. Soc. Jpn. 61: 2025–2029 (1988). However, a Patent Application to the inventor incorporated herein discloses the synthesis of (R) or (S) isomers of 3,4-dihydroxybutanoic acid (I) from substituted D- or L-pentoses. The process for the preparation of 3,4-dihydroxybutanoic acid comprises reacting a mixture of a 3-leaving group substituted-n-pental (II) selected from the group consisting of 2,4,5-trihydroxy-3-leaving group substituted-n-pental, 2,4-dihydroxy-3-leaving group 4-O-protected substituted-n-pental, 2-hydroxy-3-leaving group 4,5-di-O-protected substituted-n-pental, 4-hydroxy-3-leaving group 2,5-di-O-protected substituted-n-pental, 5-hydroxy-3-leaving group 2,4-di-O-protected substituted-n-pental, and 3-leaving group 2,4,5-tri-O-protected substituted-n-pental with a solvent containing a peroxide in the presence of a base to produce (I) and a protonated leaving group, and then separating (I) from the mixture. In this process, (I) can be produced by providing a substituted pentose (III) selected from the group consisting of 2,4,5-trihydroxy-3-R-pentose, 2,4-protected-3-R-pentose, 4-protected-3-R-pentose, 2-protected-3-R-pentose, and 5-protected-3-R-pentose in the reaction mixture wherein the substituted pentose can be a leaving group substituted furanose (IV) or a leaving group substituted pyranose (V). In a preferred embodiment (I), (II),(III), (IV) and (V) are each a single chiral compound.

In making 3,4-dihydroxybutanoic acid, the peroxide is selected from the group consisting of hydrogen peroxide, alkaline earth peroxides, and combinations thereof, and the base is selected from the group consisting of alkaline earths, alkaline metals, substituted ammonium hydroxides and combinations thereof. The selection of the peroxide and the base is well within the skill of the art. The solvent is selected from the group consisting of water and water miscible organic solvents, methanol, isopropanol, dioxane, tetrahydrofuran (THF), dimethylformamide and combinations thereof. Hydrogen peroxide and sodium hydroxide have been particularly useful.

In the preparation of chiral 3,4-dihydroxybutanoic acid, the sodium hydroxide or potassium hydroxide and the hydrogen peroxide molar concentration is between 1 to 2 fold of the total pentose which usually between 0.05% to 80% by weight per volume of the reaction mixture. The reaction of the base with the pentose is preferably conducted for at least 4 hours and preferably between 10 and 24 hours. Preferably, the reaction is conducted at a temperature between about 50° C. and 70° C.

The pentose is selected from the group consisting of D and L isomers. Examples of pentoses that can be used are arabinose, ribulose, xylose and lyxose. In particular, the pentose can be a 3-leaving group substituted pentose with a saccharide as the leaving group. Preferably, the pentose is selected from the group consisting of 3-O-methyl pentose, 3-O-alkyl-pentose, 3,4-O-alkylidene-pentose, 3,5-O-alkylidene-pentose, 2,3-O-alkylidene-pentose, 3,4-O-arylidene-pentose, 3,5-O-arylidene-pentose, 2,3-O-arylidene-pentose, 3-O-acyl-pentose, 3,4-O-acylidene-pentose, 2,3-O-acylidene-pentose, 3,5-O-acylidene-pentose, ester-substituted-pentoses and 3-O-sugar substituted-pentose wherein the sugar provides the leaving group.

Furthermore, the leaving group is selected from the group consisting of alkyloxy, aryloxy, acyloxy, halo, sulfonyloxy, sulfate, phosphate, and a saccharide and wherein (I), (II) and (IV) are each a single chiral compound. Therefore, (I) is either an (R) isomer or an (S) isomer and in a preferred embodiment the pentose is selected from the group consisting of 3-O-methyl-arabinose, 3,4-O-methyl-arabinose, 3,4-O-isopropylidene-arabinose, 3-O-galactopyranosyl-arabinose, and 2,3-O-isopropylidene-arabinose. In a most preferred embodiment the 2,4,5-trihydroxy-3-substituted-n-pentanal or other substituted pentose or furanose is a D-sugar or a L-sugar. Thus, pentose sugars can be converted to chiral 3,4-dihydroxybutanoic acid by oxidation with a peroxide source and a base if the pentose sugar is substituted at the 3-position. The reaction proceeds by oxidation with a peroxide source and a base. As long as the 3-position is substituted, the substituted sugar is converted to 3,4-dihydroxybutanoic acid.

The nature of the R group is quite variable. R can be any leaving group examples of which are alkyloxy, aryloxy, acyloxy, halo, sulfonyloxy, sulfate, or phosphate groups. The most easily obtained functionality is an alkoxy group. Hence 3-O-methyl pentoses are good substrates as are certain acetals such as 3,4-O-isopropylidene, 3,5-O-benzylidene, and 2,3-O-isopropylidene pentose acetals. Acyl and other ester substitutions and disaccharides such as 3-O-β-D-galactopyranosyl-D-arabinose are also useful substrates. Thus, in addition to pentoses having 3-leaving groups, pentoses having 3,4-leaving groups, 2,3-leaving groups and 3,5-leaving groups are all encompassed by the present invention. The dihydroxybutyric acid can be converted to the corresponding gamma-lactone by acidification with a mineral acid, concentrating and then extracting the product into an organic solvent such as ethylacetate, chloroform or tetrahydrofuran (THF). Thus, polyacetylene compounds made according to the present invention can be either exclusively (R) or (S) when compound 4 is made from (R) or (S) 3,4-dihydroxybutanoic acid.

In summary, the present invention describes compounds and processes which allowed the assembly of hydrocarbon chains containing diacetylene functions with the packing densities, orientation and long-range order necessary for forming highly conjugated 2-dimensional polymer systems. The present invention's strategy allows preparation of molecules which are analogs of bio-membrane lipids and uses their self-assembling propensity to direct and achieve the regularity of packing and the high 2-dimensional order that is required. The syntheses are characterized by brevity and very high efficiency. A series of instrumental analyses indicated that these membrane lipid mimics of the present invention have the desired properties; X-ray diffraction, laser confocal polarized light microscopy and molecular modeling all indicated that the compounds of the present invention formed well oriented lamellar films. Atomic force microscopy experiments further showed that very flat thin films were formed. Near IR study confirmed that the UV polymerized or doped films have the desired optical properties. The conjugation was exceptionally high with peak electronic transitions occurring way into the infrared spectrum. Therefore, these membrane mimics have properties that make them to be excellent building units for cast films. An unexpected property of the compounds is that in the process of using monomers of the compounds to make films there is no need for an external boundary to confine the monomers, the behavior of the system is built into the structure of the monomer. Therefore, the present invention provides a simple process for generating 2-dimensional molecular films -or networks containing diacetylene functions. The present invention will have important utility in the design of advanced materials and electro-optical devices.

The following examples are intended to promote a further understanding of the present invention.

EXAMPLE 1

This example describes the synthesis of (S) 1-N,N-dimethylaminoethyl-3,4-dihydroxybutyramide (compound. 5). The synthetic route utilizes the stereocenter in (S)-3-hydroxybutyrolactone (compound 4) as the source of chirality for compounds 1 and 2. The preparation of the lactone has been described earlier in U.S. Pat. Nos. 5,374,773,. 5,319,110, and 5,292,939 to Hollingsworth which are herein incorporated by reference.

The steps described herein have been demonstrated to preserve the stereocenter of the molecule (Huang, G., et al., Tetrahedron, 54:1355–1360 (1998)). (S)-3-hydroxybutyrolactone 51 g (0.5 mol), N,N-dimethylethylenediamine 44 g (0.5 mol), and 100 ml absolute ethanol were mixed and stirred for 24 hours. The solvent was removed by rotatory evaporation under reduced pressure. The (S) 1-N,N-dimethylaminoethyl-3,4-dihydroxybutyramide product was dried by vacuum oven for 24 hours to yield a heavy brown syrup 95 g (100%). $^1$H NMR (300 MHZ, CDCl$_3$ δ6.19 (s (broad), 1H), 4.05 (m, 1H), 3.65 (dd, 1H, J=11.4, 3.9 Hz), 3.52 (dd, 1H, J=11.4, 5.1 Hz), 3.49–3.39 (m, 1H), 3.33–3.21 (m, 1H), 2.45–2.35 (m, 4H), 2.23 (s, 6H). $^{13}$C NMR (75 MHZ, CDCl$_3$) 172.34, 69.12, 65.89, 57.83, 44.95, 39.60, 36.58. IR (NaCl window, CHCl$_3$ as solvent), 3297, 3090, 2944, 2865, 2824, 2780, 1647, 1555, 1462, 1190, 1040 cm$^{-1}$.

EXAMPLE 2

This example describes the preparation of compound 1 (FIG. 10). All reactions and workups relating to diacetylenic compounds were conducted with exclusion of light. Amber glassware was used and samples covered with aluminum foil. A photography safe light was used for illumination when conducting chromatographic separations.

In the first step, 10,12-docosadiynedinoic and 1.81 g (0.005 mol), oxalyl chloride 15 ml (0.172 mol), and dry dichloromethane 10 ml, were mixed and stirred under a dry atmosphere overnight at room temperature. The solvent and excess oxalyl chloride were quickly removed under reduced pressure by rotatory evaporation. The diacyl dihydride product (compound 6) was taken up in 5 ml hexane and rotatory evaporated to dryness to remove the last traces of oxalyl chloride.

The crude, freshly prepared (S) 1-N,N-dimethylaminoethyl-3,4-dihydroxybutyramide (compound 5 made according to Example 1) was used directly for the next reaction step. A mixture of dried compound 5 (0.95 g, 0.005 mol), 5 ml dry pyridine and 5 ml of dry dichloromethane was cooled to 0° C. in an ice bath under dry nitrogen. The acetylene dioxyhalide product (compound 6) was dissolved in 5 ml of dry dichloromethane and added to the mixture of compound 5 with a dropping funnel over a 10 minute period. The reaction mixture was then stirred for 24 hours. The solvent was removed by rotatory evaporation and the residue taken up in chloroform. The dissolved residue was washed sequentially with 0.1 N HCl, saturated sodium bicarbonate solution, and then brine. Then the organic phase was dried with anhydrous sodium sulfate. Removal of the chloroform solvent yielded as a red solid diacetylenic compound 1. The yield of compound 1 was 2.3 g (89%) which was found to be homogeneous by thin layer chromatography. $^1$H NMR (300 MHZ, CDCl$_3$) 6.41 (s (broad), 2H), 5.40 (m, 2H), 4.31 (m, 2H), 4.13 (m, 2H), 3.31 (m, 4H), 2.47 (m, 4H), 2.35–2.15 (m, 32H), 1.64–1.40 (m, 16H), 1.27 (b, 32H) C$^{13}$ NMR (75 MHZ, CDCl$_3$) 173.25, 172.73, 168.63, 68.54, 65.20, 64.27, 57.53, 44.88, 37.82, 36.51, 34.17, 33.98, 29.01, 28.86, 28.73, 28.24, 24.76, 19.12 IR (NaCl, CDCl$_3$) 2932, 2855, 1738, 1653, 1547, 1462, 1159, 621.2 Fast atom bombardment mass spectrometry (FABMS) 1033.9 (C$_{60}$H$_{96}$N$_4$O$_{10}$, NH$^+$).

EXAMPLE 3

This example describes the preparation of compound 2 (FIG. 11). The method and workup were essentially the same as described above for compound 1 with slight differences in procedure.

In the first step, 10,12-pentacosadynoic acid (2.24 g, 0.006 mol), 10 ml oxalyl chloride (0.115 mol) and dry dichloromethane 10 ml were stirred overnight at room temperature. The solvent and excess oxalyl chloride were quickly removed under reduced pressure by rotatory evaporation. The acetylene oxyhalide product (compound 7) was taken up in 5 ml hexane and rotatory evaporated to dryness to remove the last traces of oxalyl chloride.

For the esterification,(S) 1-N,N-dimethylaminoethyl-3,4-dihydroxybutyramide (compound 5) 0.475 g (0.0025 mol) was used for the reaction. A mixture of dried compound 5, 5 ml dry pyridine and 5 ml of dry dichloromethane was cooled to 0° C. in an ice bath under dry nitrogen. The acetylene oxyhalide product (compound 7) was dissolved in dry dichloromethane and added to the mixture of compound 5. The reaction mixture was then stirred for 24 hours. The crude product was purified by flash column chromatography on silica gel using chloroform:acetone:methanol (1:1:1) as the solvent. The diacetylenic compound 2 was obtained as a purple solid 1.97 g (87%) $^1$H NMR, (300 MHZ, CDCl$_3$) 6.92 (s, 1H), 5.39 (m, 1H), 4.30 (dd, 1H, J=3.6, 12.0 Hz) 4.12 (dd, 1H, J=5.8, 12Hz) 5.35 (m, 2H), 2.55–2.44 (m, 2H), 2.32–2.18 (m, 24H), 1.64–1.42 (m, 12H), 1.40–1.10 (m, 2H), 0.85 (t, J=6.6 Hz). $^{13}$C NMR (75 MHZ, CDCl$_3$), 173.30, 172.78, 168.90, 68.58, 65.27, 65.18. 64.38, 57.52, 44.50, 37.75, 36.20, 34.23, 34.03, 31.89, 29.61, 29.46, 29.33, 29.09, 28.91, 28.85, 28.78, 28.33, 24.80, 22.67, 19.18, 14.11. IR (NaCl, CHCl$_3$) 2919, 2851, 1734, 1653, 1470, 1246, 1175, 718.cm$^{-1}$. FABMS 903.7 (MH$^+$, $C_{58}H_{98}N_2O_5$). Because of their high lability to oxygen and instability to light combustion, analyses could not be obtained on these materials.

EXAMPLE 4

This example describes making films using compound 1 or 2 and analyzing the properties of the films thus formed by infrared (IR) spectroscopy.

Compound 1 or 2 was dissolved in chloroform to give an approximately 1% solution. A few drops of the clear solution was transferred by a Pasteur pipette onto clean microscope slides. The solution which spread across the slide, evaporated leaving behind a film layer. The film was -either polymerized by irradiation with UV light (254 nm, 6 Watts, 350 μWatts per cm$^2$ for 3 minutes) or the film layer was doped by holding the slide in a horizontal position about 10–15 cm above some iodine crystals at room temperature. In the UV polymerization experiment, the light yellow to colorless film turned to blue after UV irradiation. In contrast, the films turned yellow-orange after doping with iodine.

Near IR experiments were performed using diode array spectrometers from Control Data (South Bend, Ind.). The films were irradiated using a tungsten source and the slides were placed directly in the light path. FIGS. 9A to 9H are near IR spectra of films formed from compound 1 (FIGS. 9A to 9D) and compound 2 (FIGS. 9E to 9H). In A, B, E, F, the films were polymerized by UV irradiation and in C, D, G, H, the films were iodine doped. Spectra on the left were acquired in the range of 600–1050 nm, and those to the right were acquired between 880 and 1700 nm.

The near IR results show that compounds 1 or 2 polymerized as shown above have optical properties that are desirable and similar.

EXAMPLE 5

This example demonstrates formation of films of either compound 1 or 2 and the properties of the films thus formed using atomic force microscopy (AFM). The AFM analyses were performed using a Nanoscope III instrument which was operating in contact mode. For these measurements, compound 1 or 2 were dissolved in chloroform-methanol (0.5–1% solutions) and ~10 μL was transferred to freshly cleaved mica plates spinning at 200 rpm. The rotation of the mica plates facilitated even film spreading and evaporation.

Figure 5A:
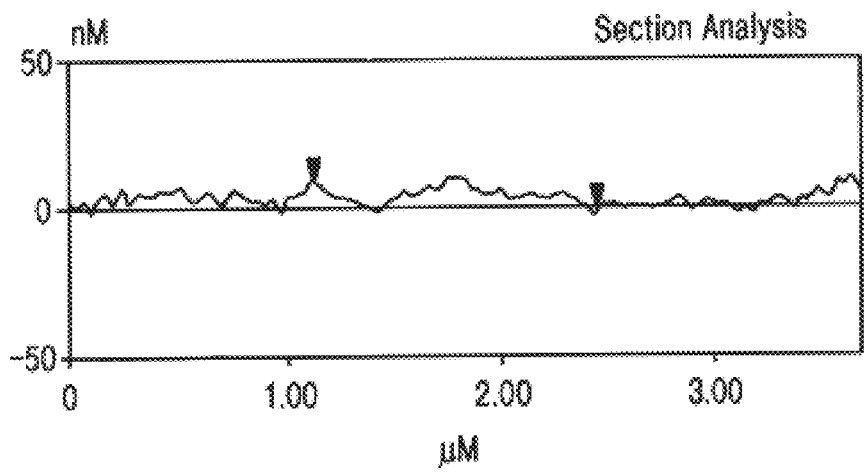
FIGS. 5A, 5B and 5C relate to atomic force microscopy (AFM) images. AFM images of a film formed by compound 1 on a freshly-cleaned mica surface.
Figure 5B:
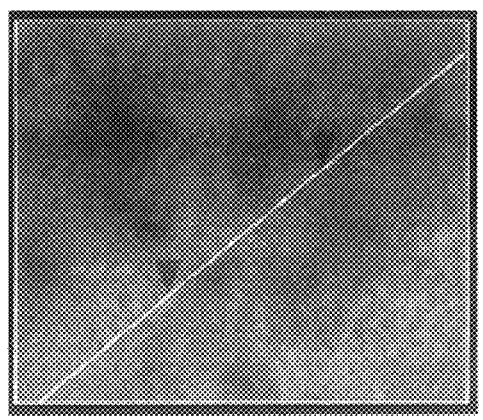
Figure 5C:
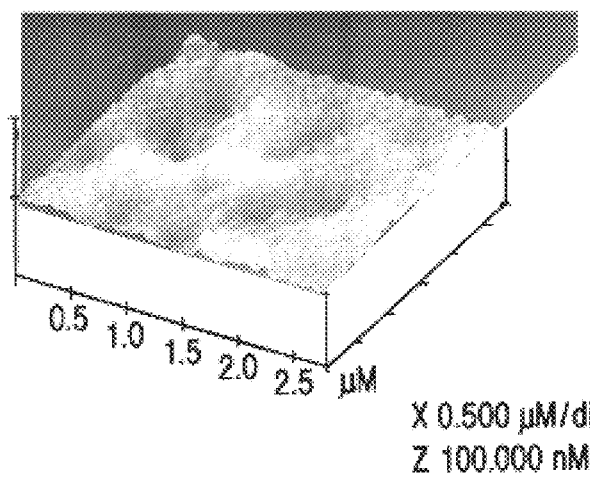
Figure 6A:
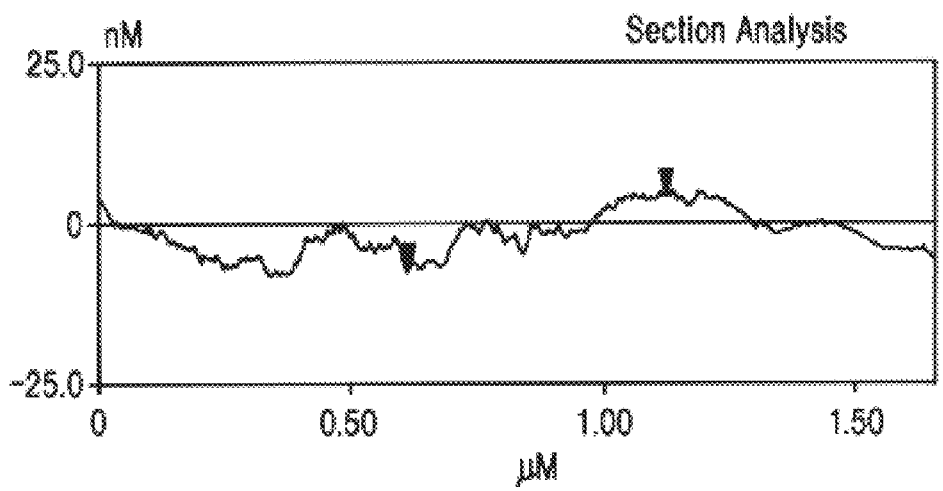
FIGS. 6A, 6B and 6C are AFM images of a film formed by compound 2 on a freshly-cleaned mica surface.
Figure 6B:
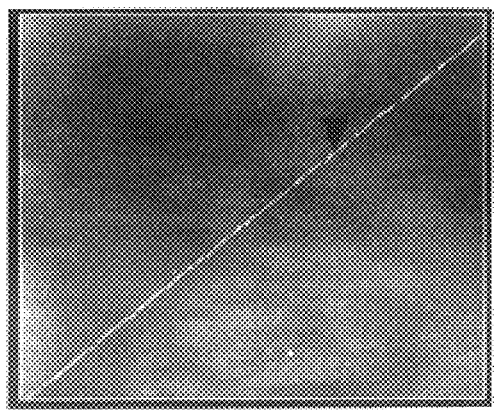
Figure 6C:
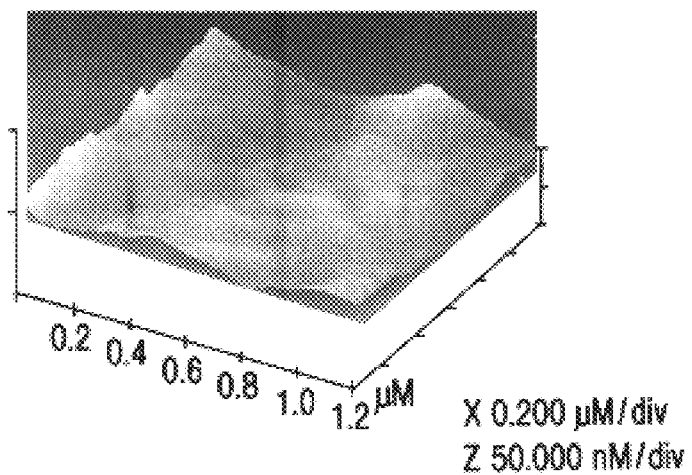

FIGS. 5A, 5B and 5C show AFM images of a film formed by compound 1 on a freshly-cleaned mica surfaces. FIG. 5A shows a sectional analysis of the film conducted over a 4 μM length. FIG. 5B is a top view of the same area shown in FIG. 5A. FIG. 5C is a perspective surface plot of the same area shown in FIG. 5B. FIGS. 6A, 6B and 6C are AFM images of a film formed by compound 2 on a freshly-cleaned mica surface. FIG. 6A shows a sectional analysis of the film conducted over a 2 μM length. FIG. 6B shows a top view of the same area shown in FIG. 6A. FIG. 6C is a perspective surface plot of the same area shown in FIG. 6B.

The AFM analysis showed that the films were very flat and thin. In particular, compound 1 had a surface variation of only 9.85 nm over a distance of 1331 nm (0.7%) and compound 2 had a surface variation of 12 nm over a distance of 512 nm (2.3%).

EXAMPLE 6

This example demonstrates formation of films of either compound 1 or 2 and the properties of the films thus formed using Laser scanning confocal light microscopy. These experiments were performed on a Zeiss 210 instrument with a 488 nm laser. Images were obtained in the bright field, dark-field, phase contrast and polarization modes. For the polarizing mode experiments, an analyzing cross-polarizer was placed on the objective lens and rotated until light cancellation. For film preparation, compound 1 or 2 was dissolved in a 4:1 ethanol:water mixture, and a few drops of solution were deposited on clean glass slides which were left in a horizontal position at 30–40° C. for two hours to allow the solvent to evaporate.

FIGS. 7A, 7B, 7C and 7D are laser scanning confocal micrographs of hydrated films of compound 1 (7A and 7B) and compound 2 (7C and 7D). The images on the left (FIGS. 7A, 7C) were acquired using cross polarizers and the images to the right (FIGS. 7B and 7D) were obtained using dark field optics. The films are the areas to the right of the fields. These results show that films composed of either compound 1 or 2 were highly ordered structures, with only a few point defects. The only significant defects were found at the fringes of the films which was because of the edges of the films were bent in contact with the glass.

EXAMPLE 7

This example demonstrates formation of films of either compound 1 or 2 and the properties of the films thus formed using X-ray diffraction. These studies were performed on a Rigaku instrument with a Rotaflex rotating copper anode operating at 45 kV with a current of 100 mA. The X-ray beam was collimated with a ⅙ slit and the Kα line was selected. Compound 1 or 2 was dissolved in a minimum volume of ethanol and ¼ to ⅓ the volume of water added so that an overall 20% cloudy but uniform dispersion of sample was obtained. The samples were sonicated and vortexed several times to ensure uniformity of distribution and then sealed in glass capillaries and diffraction data obtained.

X-ray powder diffraction information for compounds 1 and 2 was used to make molecular models for films comprised of either compound which are shown in FIG. 8.

EXAMPLE 8

Molecular Mechanics Calculations of compounds 1 and 2 and films composed of compounds 1 or 2 were performed using the MM3 forcefield (Allinger, N. L., et al., J. Amer. Chem. Soc. 111:8551–8566 (1989)) as implemented in the program Alchemy (Tripos, Inc., St. Louis, Mo. 63144 USA). Minimizations were performed using the conjugate gradient method. The parameters were used without modification since the MM3 forcefield is parametized to very accurately reproduce the geometries and heats of formation of hydrocarbons.

EXAMPLE 9

This example shows various methods for preparing compound 4 which is either (R) chiral or (S) chiral using substituted pentose sugars.

Preparation of (R)-3-hydroxy-γ-butyrolactone. 3,4-O-isopropylidene-L-arabinose (30 grams) was treated with 2700 ml of 0.36% sodium hydroxide and 27 grams of 30% hydrogen peroxide. The mixture was heated at 65° C. for 10 hours. Afterwards, the reaction was extracted with one volume of ethyl acetate, concentrated to a syrup and acidified to pH 1 with 6 M sulfuric acid, and the acidified syrup concentrated at 40° C. until no more solvent was removed. Then the syrup was extracted with 1.5 liters of ethyl acetate. The ethyl acetate layer was concentrated to yield 15.5 grams (96%) of (R)-3-hydroxy-γ-butyrolactone. The product was greater than 90% pure as judged by gas chromatography. Chiral GC analysis on a cyclodextrin phase showed that there was greater than 99.8% of the (R)-3-hydroxy-γ-butyrolactone product.

Preparation of (R)-3-hydroxy-γ-butyrolactone using 3,4-O-methyl-L-arabinose. 3,4-O-methyl-L-arabinose (30 grams) was treated with 2700 ml of 0.36% sodium hydroxide and 27 grams of 30% hydrogen peroxide. The mixture was heated at 65° C. for 10 hours. Afterwards, the reaction was extracted with one volume of ethyl acetate, concentrated to a syrup and acidified to pH 1 with 6 M sulfuric acid, and the acidified syrup concentrated at 40° C. until no more solvent was removed. Then the syrup was extracted with 1.5 liters of ethyl acetate. The ethyl acetate layer was concentrated to yield 95% (R)-3-hydroxy-γ-butyrolactone. The product was greater than 95% pure as judged by gas chromatography. The optical purity was greater than 99.8%.

Preparation of (S)-3-hydroxy-γ-butyrolactone using 3-O-β-D-galactopyranosyl-D-arabinose. 3-O-β-D-galactopyranosyl-D-arabinose (30 grams) was treated with 2700 ml of 0.36% sodium hydroxide and 27 grams of 30% hydrogen peroxide. The mixture was heated at 65° C. for 10 hours. Afterwards, the reaction was extracted with one volume of ethyl acetate, concentrated to a syrup and acidified to pH 1 with 6 M sulfuric acid, and the acidified syrup concentrated at 40° C. until no more solvent was removed. Then the syrup was extracted with 1.5 liters of ethyl acetate. The ethyl acetate layer was concentrated to yield 85% (R)-3-hydroxy-γ-butyrolactone. The product was greater than 90% pure as judged by gas chromatography. The optical purity was greater than 99.8%.

Preparation of (S)-3-hydroxy-γ-butyrolactone using 2,3-O-isopropylidene-D-arabinose. 2,3-O-isopropylidene-D-arabinose (30 grams) was treated with 2700 ml of 0.36% sodium hydroxide and 27 grams of 30% hydrogen peroxide. The mixture was heated at 65° C. for 10 hours. Afterwards, the reaction was extracted with one volume of ethyl acetate, concentrated to a syrup and acidified to pH 1 with 6 M sulfuric acid, and the acidified syrup concentrated at 40° C. until no more solvent was removed. Then the syrup was extracted with 1.5 liters of ethyl acetate. The ethyl acetate layer was concentrated to yield 60% (S)-3-hydroxy-γ-butyrolactone. The product was greater than 85% pure as judged by gas chromatography. The optical purity was greater than 99.8%.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A process for producing a film of monomers of ordered polydiacetylene with two side-by-side carbon chains and aligned diacetylene groups in each chain which comprises:
    (a) reacting a 1-N,N-dialkylaminoalkyl-3,4-dihydroxyalkyl amide with an acyl halide in a reaction mixture to produce 1-N,N-dialkylamino-3,4-di(acetyleneoxy group)alkylamide as the ordered polydiacetylene compound, wherein alkyl in the dialkyl amino is between 1 to 6 carbon atoms and the acetyleneoxy group is between 6 to 50 carbon atoms in a linear alkylene chain with the diacetylene groups;
    (b) separating the ordered compound from the reaction mixture; and
    (c) depositing the compound on a substrate to form a two-dimensional structure.

2. The process of claim 1 wherein the acyl halide is a diacyl dihalide and wherein the ordered polyacetylene compound has two alkyl amide groups positioned at each of the opposed ends of the diacetylene dioxy group.

3. A process for producing a film of monomers of ordered polydiacetylene with two side-by-side chains and aligned diacetylene groups in each chain which comprises:
    (a) reacting a single chiral 1-N,N-dimethylaminoethyl-3,4-dihydroxybutyramide with an acyl halide in a reaction mixture to produce 1-N,N-dimethyl amino-3,4-di(diacetyleneoxy group)butyramide as the ordered polydiacetylene compound;
    (b) separating the ordered polydiacetylene compound from the reaction mixture; and
    (c) depositing the polydiacetylene compound on a substrate to form a two-dimensional structure.

4. The process of claim 3 wherein the acyl halide is a diacyl dihalide and wherein the ordered polyacetylene has two alkylamide groups positioned at each of the opposed ends of acetylene dioxy group.

5. A process for producing a film of monomers of ordered polyacetylene with two side-by-side carbon chains and aligned acetylene groups in each chain which comprises:
    (a) reacting a 1-N,N-dialkylaminoalkyl-3,4-dihydroxyalkyl amide with an acyl halide in a reaction mixture to produce 1-N,N-dialkylamino-3,4-di(acetyleneoxy group)alkylamide as the ordered polyacetylene compound, wherein alkyl in the dialkyl amino is between 1 to 6 carbon atoms and the acetyleneoxy group is between 6 to 50 carbon atoms in a linear alkylene chain with the acetylene groups;
    (b) separating the ordered polyacetylene compound from the reaction mixture; and
    (c) depositing the polyacetylene compound on a substrate to form the two-dimensional polymer structure.

* * * * *